Oct. 19, 1965 D. H. MOREY, JR Plant Pat. 2,558
ROSE PLANT
Filed Oct. 9, 1963
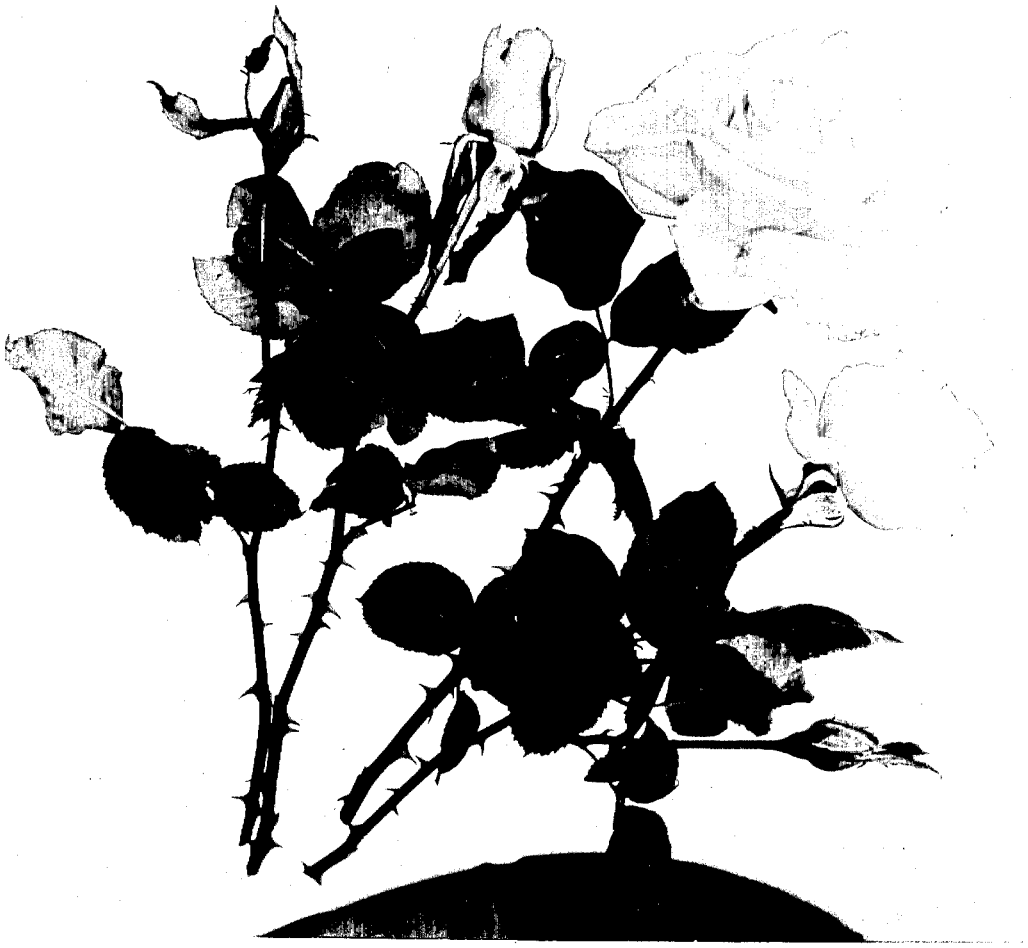
INVENTOR:
DENNISON H. MOREY, JR.
BY Rummler & Snow
ATT'YS United States Patent Office Plant Pat. 2,558
Patented Oct. 19, 1965

2,558
ROSE PLANT

Dennison H. Morey, Jr., Pleasanton, Calif., assignor to Jackson and Perkins Company, Inc.

Field Oct. 9, 1963, Ser. No. 315,097
1 Claim. (Plt.—20)

This disclosure concerns a new and distinct variety of hybrid-tea rose plant developed by me at Pleasanton, California in 1954 as a result of breeding efforts carried on by me at Pleasanton, California and at Livermore, California since 1951.

The main objective of the said breeding efforts was to produce a rose plant having the growing and flowering habit of "New Yorker" (Plant Patent 823), including its flower form and weatherability, and the richer—more sunfast—color of "Mardi Gras" (Plant Patent 1,139), a particular purpose being to lessen the tendency of the blooms of "New Yorker" to "blue" upon aging and to increase its fragrance.

These improved characteristics were all found to be present in my new variety, which was originated as a seedling of "Mardi Gras" for which the pollen parent was "New Yorker," and asexual reproduction of the new variety by budding, at Livermore, California, has demonstrated that all of these characteristics are fixed and remain true from generation to generation.

The accompanying drawing shows details of my new variety of rose plant and illustrates in general its distinctive characteristics, the view including representative foliage as well as a bud, a partly opened bloom and a fully opened bloom, all in full color.

The following is a detailed description of my new variety of rose plant, the color designations being according to the Horticultural Color Chart of the Royal Horticultural Society.

*The plant*

Origin: Seedling.
Parentage:
*Seed parent.*—"Mardi Gras" (P.P. 1,139).
*Pollen parent.*—"New Yorker" (P.P. 823).
Classification: Hybrid tea.
Form: Bush.
Growth: Vigorous, sturdy, strong and upright.
Height: 20 to 30 inches.
Branching: Moderate.
Foliage:
*Quantity.*—Abundant.
*Shape of leaf.*—Odd pinnate.
*Number of leaflets.*—3 to 7, average 5.
*Shape of leaflets.*—Generally ovate with pointed tip and serrated margins.
*Size of leaflets.*—2 inches wide x 4 inches long.
*Texture.*—Smooth, leathery, semi-glossy.
*Color.*—Upper side—Spinach Green (0960). Under side—Lavender Green (000761).
*Petioles.*—Length, 1".
*Ribs and veins.*—Conspicuous.
*Plant has thorns and prickles.*—Color: young thorns—red at base, green tip; mature thorns—straw to tan. Size.—¼ inch to ⅜ inch.

*The flower bud*

Form: Long and pointed—becoming urceolate.
Size: Medium.
*Length.*—1 to 1½ inches.
*Diameter.*—¾ to 1⅛ inches.
Opens slowly.
Color:
*When sepals first divide.*—Blood Red (820–821).
*When sepals begin to unfurl.*—Blood Red (820–821).

Sepals: Strongly appendaged, curl back as they unfurl; not branched. Color: inside — Lavender Green (000761); outside—Spinach green (0960).
Hypanthium:
*Shape.*—Funnelform.
*Size.*—Medium, ⅜ inch wide and ¼ inch long.
*Aspect.*—Outside, smooth; inside, hairy.
Peduncle:
*Length.*—2½ to 3 inches. Strong, erect and has some prickles.
*Color.*—Spinach Green (0960).

*The flower*

Blooming habit: Recurrent. Intermittent but nearly continuous. Plant blooms profusely from spring through fall.
Borne: Singly. Occasionally two or three on strong canes.
Size: Medium.
*Diameter.*—4–5 inches.
*Depth.*—1½ to 2 inches.
Shape: High centered when bloom first opens. Flattens somewhat as bloom matures.
Pedals:
*Arrangement.*—Imbricated.
*Number of petals.*—20 to 25.
*Form.*—Obovate.
*Texture.*—Almost leathery.
*Appearance.*—Velvety.
*Color.*—Outer petal—Rose Red, overlaid with Blood Red (724+820). Inside petal — Blood Red (820) turning to Magenta tone (727) after 3 days. Reverse side—Blood Red to Magenta (820+27) becoming Tyrian Purple (727) after 3 days.
*Discoloration (after full bloom).*—Slight bluing and fading.
*Persistence.*—7 to 10 days on stem.
Petaloids:
*Number.*—5 to 10.
*Size.*—½ to 1 inch.
*Color.*—Like petals. Sometimes, but very rarely, streaked.
Peduncle: Sturdy and upright.
*Length.*—2½ to 3 inches.
*Color.*—Spinach Green (0960).
Fragrance: Moderate, tea rose fragrance.
Effect of weather: Resistant to affection by wet and hot weather.
Disease resistance: Average resistance to mildew, rust, and blackspot as observed at Livermore, California.
Lasting quality: 7 to 10 days on the plant. 4 to 6 days as a cut flower.

*Genital organs*

Stamens:
*Anthers.*—Plus or minus 120 in number, ½ inch long. Whorled arrangement.
*Filaments.*—7/16 inch long. Yellow tinted red in color.
Pollen: Yellow-orange.
Pistils: Plus or minus 56 in number. ¼ inch, plus or minus, in length.
Stigmas: Color—ivory white.
Ovaries: Of ordinary character.

*Fruit*

Fertility: Partially fertile.
Shape: Funnelform rounded.
Color at maturity: Orange.

My new variety of rose plant most resembles its pollen parent "New Yorker." It differs from "New Yorker,"

however, by the richer, velvety red color, of its blooms, its fragrance and its resistance to "bluing" with age. The new variety is further distinguished from "New Yorker" by its upright habit of growth and by its longer, more slender, pointed buds.

The new variety differs from its seed parent "Mardi Gras" by its more profuse branching and by its stronger peduncle and larger size of flower. The new variety is distinguished from both of its parents, and from most other rose plants, by the size of its sepal appendages which may become 1½ to 2 inches long and ½ inch wide at the point of attachment thus giving the bud a crested or flagged effect. It is similar to "Avon" (Plant Patent 2,154) in color and bud form but is believed to improve on that variety by the upright habit and vigor of its growth and the neater imbrication of its petals.

The new variety of rose plant is particularly outstanding for its tolerance of flower cutting and the rapidity with which new growth and blooms are initiated after the flowers have been cut or have gone by.

Having thus described my new variety of rose plant, I claim:

A new and distinctive variety of rose plant, substantially as shown and described, particularly characterized by the rich blood red color of its blooms which are substantially resistant to bluing upon aging and which are resistant to deleterious effects of weather; by the relatively large size of the sepal appendages; and by its tolerance of flower cutting and the rapid rate at which new growth and blooms are produced after the flowers are cut.

No References Cited.